(12) United States Patent
Lee et al.

(10) Patent No.: US 10,660,803 B2
(45) Date of Patent: May 26, 2020

(54) ABSORBENT ARTICLE WITH MULTI-USE PROTECTION LAYER

(71) Applicant: Kimberly-Clark Worldwide, Inc, Neenah, WI (US)

(72) Inventors: KyuLe Lee, Seongnam-si (KR); Junghyun Park, Seongnam-si (KR); Franz Aschenbrenner, Kastl (DE); SeongDae Roh, Yongin-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 589 days.

(21) Appl. No.: 15/506,186

(22) PCT Filed: Aug. 28, 2014

(86) PCT No.: PCT/US2014/053126
§ 371 (c)(1),
(2) Date: Feb. 23, 2017

(87) PCT Pub. No.: WO2016/032481
PCT Pub. Date: Mar. 3, 2016

(65) Prior Publication Data
US 2017/0239102 A1 Aug. 24, 2017

(51) Int. Cl.
*A61F 13/474* (2006.01)
*A61F 13/56* (2006.01)
(Continued)

(52) U.S. Cl.
CPC ............ *A61F 13/474* (2013.01); *A61F 13/53* (2013.01); *A61F 13/5611* (2013.01);
(Continued)

(58) Field of Classification Search
CPC . A61F 13/474; A61F 13/84; A61F 2013/8497
See application file for complete search history.

(56) References Cited

U.S. PATENT DOCUMENTS 3,688,771 A 9/1972 Werner
4,336,804 A 6/1982 Roeder
(Continued)

FOREIGN PATENT DOCUMENTS

CN 101283942 A 10/2008
CN 101534771 A 9/2009
(Continued)

*Primary Examiner* — Adam Marcetich
*Assistant Examiner* — Jessica R Arble
(74) *Attorney, Agent, or Firm* — Kimberly-Clark Worldwide, Inc.

(57) ABSTRACT

An absorbent article which can be more readily adaptable to meet the needs of the individual wearer of the absorbent article. The absorbent article can have a topsheet layer, a backsheet layer, and an absorbent core between the topsheet layer and the backsheet layer. The backsheet layer can have a garment attachment mechanism located on a garment facing surface of the backsheet layer. The absorbent article can further have a protection layer situated over and engaged with the garment attachment mechanism. The protection layer can be capable of being at least partially dis-engaged from the garment attachment mechanism. The protection layer of the absorbent article can be utilized by the wearer to provide additional area of coverage as deemed suitable by the wearer of the absorbent article.

12 Claims, 7 Drawing Sheets

(51) Int. Cl.
*A61F 13/53* (2006.01)
*A61F 13/84* (2006.01)

(52) U.S. Cl.
CPC ......... *A61F 13/5616* (2013.01); *A61F 13/84* (2013.01); *A61F 2013/530029* (2013.01); *A61F 2013/530481* (2013.01); *A61F 2013/530868* (2013.01); *A61F 2013/8497* (2013.01)

(56) References Cited

U.S. PATENT DOCUMENTS

| | | | |
|---|---|---|---|
| 4,596,570 A * | 6/1986 | Jackson | A61F 13/4704 604/387 |
| 4,597,759 A | 7/1986 | Johnson | |
| 5,037,418 A | 8/1991 | Kons et al. | |
| 5,087,254 A | 2/1992 | Davis et al. | |
| 5,562,651 A | 10/1996 | Ahr | |
| 5,591,153 A | 1/1997 | Mattingly, III | |
| 5,599,339 A | 2/1997 | Horney | |
| 5,670,004 A | 9/1997 | Mattingly, III | |
| 5,694,739 A | 12/1997 | Mattingly, III | |
| 5,704,929 A | 1/1998 | Bien | |
| 5,718,699 A | 2/1998 | Brisebois | |
| H1788 H | 2/1999 | Christon et al. | |
| 6,595,977 B1 | 7/2003 | Luizzi, Jr. et al. | |
| 2002/0026167 A1 * | 2/2002 | Pompa | A61F 13/474 604/378 |
| 2002/0143311 A1 * | 10/2002 | Brisebois | A61F 13/474 604/385.01 |
| 2002/0143316 A1 | 10/2002 | Sherrod et al. | |
| 2003/0149417 A1 | 8/2003 | Kudo | |
| 2004/0249356 A1 | 12/2004 | Bell et al. | |
| 2005/0124960 A1 | 6/2005 | Ruman | |
| 2005/0131372 A1 | 6/2005 | Wheeler et al. | |
| 2008/0009818 A1 | 1/2008 | Rubio | |
| 2009/0276934 A1 | 11/2009 | Lindsay et al. | |
| 2011/0257619 A1 | 10/2011 | Tosado et al. | |
| 2012/0296303 A1 * | 11/2012 | Ng | A61F 13/47263 604/378 |

FOREIGN PATENT DOCUMENTS

| | | | |
|---|---|---|---|
| CN | 101534774 A | 9/2009 | |
| CN | 101959484 A | 1/2011 | |
| GB | 2 298 627 A | 9/1996 | |
| WO | WO 2002/045639 A1 | 6/2002 | |
| WO | WO 2012/132488 A1 | 10/2012 | |
| WO | WO-2012132488 A1 * | 10/2012 | ......... A61F 13/4702 |
| WO | WO 2013/095227 A1 | 6/2013 | |

* cited by examiner

ABSORBENT ARTICLE WITH MULTI-USE PROTECTION LAYER

BACKGROUND

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or backsheet layers.

These commercial products, however, suffer from certain drawbacks. For example, the inner crotch portion of an undergarment, to which these products are adhered, is continually distorted, twisted and stretched due to the dynamics of the wearer of the product. As a result, the product may detach from the undergarment causing the undesirable consequence of the product moving out of place. Furthermore, while the product frequently reattaches to the undergarment, the reattachment often places the product in an undesirable position wherein the product will no longer function properly.

Additionally, while attempts have been made to design such products to provide a better contoured fit in the perineal area, one of the difficulties in attempting to design such a product is that women have an almost infinite variety of body shapes and muscle tone in the upper thigh region and, therefore, products which may provide superior comfort and protection for some women due to their configuration, may actually be deficient in these characteristics when worn by women with a different body type.

It has also been recognized that a certain percentage of the female population have an extremely heavy flow during certain portions of the menstrual cycle. Additionally, some women may have heavy menstrual discharge early in the morning due to retention of menses during sleep and a sudden discharge upon awakening. Women may also experience leakage of body exudates from the back of the product, such as when sleeping, which can occur when the body exudates moves backward along the body towards an area where coverage is not being provided by the product. Current commercial products can be deficient in providing the area of coverage that a woman may feel is necessary to provide sufficient protection against leakage and staining.

While such feminine care products are widely used, leakage of body exudates remains a top ranked concern among wearers of such products. Such leakage can result in staining of undergarments, outer garments, and/or bedsheets which is unacceptable to the wearer. Conventional products have attempted to address the concern of product leakage through a variety of efforts such as by adding additional absorbent layers to the feminine care product. Conventional products, however, have not provided the desired combination of comfort, versatility and leakage protection. For example, conventional products have not been able to deliver a high level of protection against leakage without the additional discomfort of providing a larger or bulkier feminine care product. A wearer, such as, for example, a woman responding to her level of menstrual flow, may, therefore, resort to utilizing multiple different products throughout the duration of time during which a need exists for an absorbent product.

As a result, there remains a need for an improved product, such as an absorbent article, that is more readily adaptable and which can provide additional coverage as needed by the individual wearer.

SUMMARY

In various embodiments, an absorbent article can have a first longitudinal length and a first transverse width; a topsheet layer; a backsheet layer having a garment facing surface, wherein the garment facing surface can have thereon a garment attachment mechanism; an absorbent core between the topsheet layer and the backsheet layer; a pair of opposing longitudinal direction side edges and a pair of opposing transverse direction end edges; a protection layer having a liquid impermeable layer, a liquid permeable layer, a pair of opposing longitudinal direction side edges and a pair of opposing transverse direction end edges, and wherein the protection layer is engaged with the garment attachment mechanism located on the garment facing surface of the backsheet layer; and a first configuration capable of converting to a second configuration, wherein the protection layer can be at least partially dis-engaged from the garment attachment mechanism located on the garment facing surface of the backsheet layer in the conversion of the absorbent article from the first configuration to the second configuration. In various embodiments, when the absorbent article is in the first configuration, the liquid impermeable layer is in a facing relationship with the backsheet layer and the liquid permeable layer faces away from the backsheet layer. In various embodiments, the protection layer further has an absorbent material between the liquid permeable layer and the liquid impermeable layer. In various embodiments, the conversion from the first configuration to the second configuration can increase the first longitudinal length to a second longitudinal length. In various embodiments, the conversion from the first configuration to the second configuration can increase the first transverse width to a second transverse width. In various embodiments, the liquid impermeable layer of the protection layer has thereon a garment attachment mechanism. In various embodiments, the backsheet layer further has a placement cue. In various embodiments, the backsheet layer further has an extension cue. In various embodiments, the protection layer has an open area. In various embodiments, the protection layer further has a tab. In various embodiments, the protection layer further has at least one indicator line. In various embodiments, the protection layer is capable of being folded at the at least one indicator line in the conversion of the absorbent article from the first configuration to the second configuration. In various embodiments, the protection layer is capable of being fully dis-engaged from the garment attachment mechanism and re-positioned with the absorbent article along one of the transverse direction end edges of the absorbent article. In various embodiments, the protection layer is capable of being re-positioned with the absorbent article such that one of the longitudinal direction side edges of the protection layer is adjacent one of the transverse direction side edge of the absorbent article. In various embodiments, the protection layer is capable of being re-positioned with the absorbent article such that one of the transverse direction side edges of the protection layer is adjacent one of the transverse direction end edges of the absorbent article.

DETAILED DESCRIPTION

Figure 1:
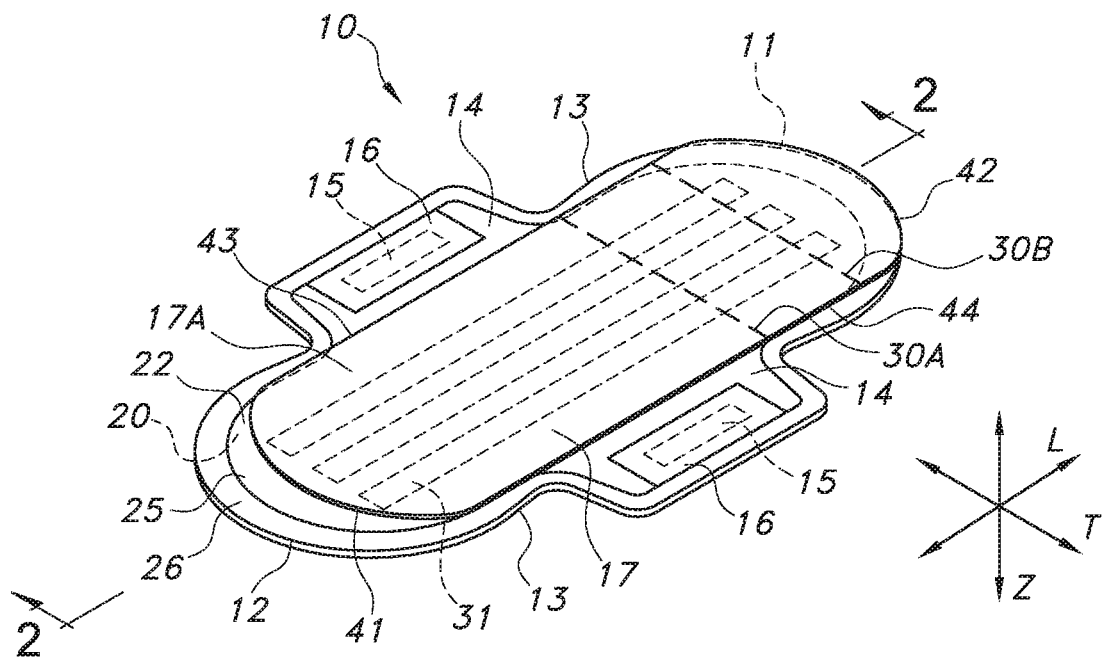
FIG. 1 is a bottom perspective view of an exemplary embodiment of an absorbent article in an embodiment of a first configuration.

The present disclosure is generally directed towards a product, such as an absorbent article, which can be more readily adaptable to meet the needs of the individual wearer of the absorbent article. The absorbent article can have a topsheet layer, a backsheet layer, and an absorbent core between the topsheet layer and the backsheet layer. The backsheet layer can have a garment attachment mechanism located on a garment facing surface of the backsheet layer. The absorbent article can further have a protection layer situated over and engaged with the garment attachment mechanism. The protection layer can be capable of being at least partially dis-engaged from the garment attachment mechanism. The protection layer of the absorbent article can be utilized by the wearer to provide additional area of coverage as deemed suitable by the wearer of the absorbent article.

The absorbent article can have a first configuration (which may in some cases be a pre-use configuration) in which the absorbent article can have a first longitudinal length and a first transverse width. Prior to usage of the absorbent article, and dependent upon their needs which they intend to be addressed by the absorbent article, the wearer of the absorbent article can manipulate the absorbent article, such as by manipulating the protection layer, and convert the absorbent article from the first configuration to a second configuration. In various embodiments, the conversion of the absorbent article from a first configuration to a second configuration can alter at least one of the first longitudinal length and/or first transverse width (in at least one region of the absorbent article) to a second longitudinal length and/or second transverse width.

In various embodiments, such as, for example, in a situation in which the wearer has no desire or need for additional area of coverage beyond the area of coverage already provided by the absorbent article itself, the conversion of the absorbent article from a first configuration to a second configuration can include the steps of fully dis-engaging the protection layer from the garment attachment mechanism of the absorbent article and disposing of the protection layer. Following the complete dis-engagement and disposal of the protection layer, the absorbent article, in the second configuration, can have a second longitudinal length and a second transverse width which, in such embodiments, are the same as the first longitudinal length and the first transverse width of the absorbent article in the first configuration.

In various embodiments, the conversion of the absorbent article from a first configuration to a second configuration can include the steps of dis-engaging a portion of the protection layer from the garment attachment mechanism of the absorbent article and folding the dis-engaged portion of the protection layer over the portion of the protection layer which remains engaged with the garment attachment mechanism. In such embodiments, at least a portion of the dis-engaged portion of the protection layer can extend beyond a transverse direction end edge of the absorbent article. In such embodiments, the portion of the dis-engaged portion of the protection layer extending beyond the transverse direction end edge of the absorbent article can increase the first longitudinal length of the absorbent article to a second longitudinal length and, therefore, the second longitudinal length of the absorbent article can be greater than the first longitudinal length of the absorbent article.

In various embodiments, the conversion of the absorbent article from a first configuration to a second configuration can include the steps of fully dis-engaging the protection layer from the garment attachment mechanism of the absorbent article and re-positioning the protection layer to the absorbent article by aligning the longitudinal direction of the protection layer with the longitudinal direction of the absorbent article and re-positioning the protection layer with the absorbent article such that a transverse direction end edge of the protection layer is positioned adjacent to a transverse direction end edge of the absorbent article. The full longitudinal length of the protection layer, therefore, is re-positioned beyond the transverse direction end edge of the absorbent article thereby increasing the first longitudinal length of the absorbent article to a second longitudinal length. The second longitudinal length is thus greater than the first longitudinal length of the absorbent article.

In various embodiments, the conversion of the absorbent article from a first configuration to a second configuration can include the steps of fully dis-engaging the protection layer from the garment attachment mechanism of the absorbent article, orienting the longitudinal direction of the protection layer perpendicular to the longitudinal direction of the absorbent article and re-positioning the protection layer with the absorbent article such that a longitudinal direction side edge of the protection layer is positioned adjacent to a transverse direction end edge of the absorbent article. The protection layer, therefore, is re-positioned beyond the transverse direction end edge of the absorbent article and is perpendicular to the absorbent article. Such a re-engagement of the protection layer can result in a second longitudinal length of the absorbent article which is greater than the first longitudinal length and a second transverse width of the absorbent article, in at least the region of the re-engagement of the protection layer to the absorbent article, which is greater that the first transverse width in the same region of the absorbent article.

Definitions:

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. The SAP ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Absorbent Article:

The absorbent article described herein can be adaptable to meet the needs of an individual wearer of the absorbent article. The absorbent article can have a topsheet layer, a backsheet layer, and an absorbent core between the topsheet layer and the backsheet layer. The backsheet layer can have a garment attachment mechanism located on a garment facing surface of the backsheet layer. The absorbent article can further have a protection layer situated over and engaged with the garment attachment mechanism. The protection layer can be capable of being at least partially dis-engaged from the garment attachment mechanism. The protection layer of the absorbent article can be utilized by the wearer to provide additional area of coverage as deemed suitable by the wearer of the absorbent article.

The absorbent article can have a first configuration in which the absorbent article can have a first longitudinal length and a first transverse width. Prior to usage of the absorbent article, and dependent upon their needs which they intend to be addressed by the absorbent article, the wearer of the absorbent article can manipulate the absorbent article, such as by manipulating the protection layer, and convert the absorbent article from the first configuration to a second configuration. In various embodiments, the conversion of the absorbent article from the first configuration to the second configuration can alter at least one of the first longitudinal length and/or first transverse width (in at least one region of the absorbent article) to a second longitudinal length and/or second transverse width.

Figure 2:
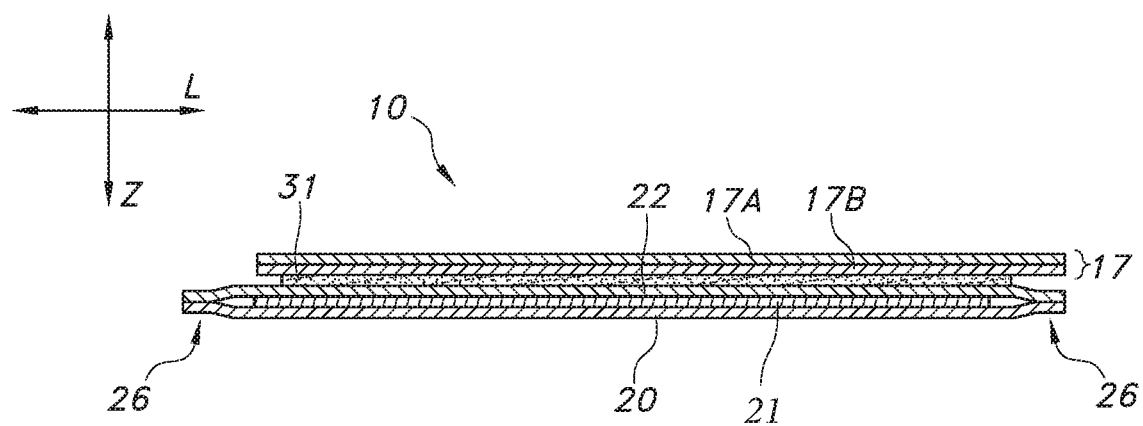
FIG. 2 is a cross-sectional view of the absorbent article of FIG. 1 taken along line 2-2.

FIG. 1 provides an illustration of a bottom perspective view of an exemplary embodiment of an absorbent article 10 in a first configuration. FIG. 2 provides a cross-sectional view of the absorbent article 10 of FIG. 1 taken along line 2-2. The absorbent article 10 can have a longitudinal direction (L), a transverse direction (T), and a depth direction (Z). The absorbent article 10 can have a first transverse direction end edge 11, a second transverse direction end edge 12 opposite the first transverse direction end edge 11, and a pair of opposing longitudinal direction side edges 13. The absorbent article 10 can have a garment facing, liquid impermeable backsheet layer 22 and a wearer facing, liquid permeable topsheet layer 20. An absorbent core 21 can be positioned between the backsheet layer 22 and the topsheet layer 20 (such as illustrated in FIG. 2). In various embodiments, the absorbent article 10 can take on various geometries but will generally have a pair of opposing longitudinal direction side edges 13 and a pair of opposing transverse direction end edges 11 and 12. As illustrated in FIGS. 1 and 2, the absorbent article 10 can have a first configuration. In various embodiments, in a first configuration, the absorbent article 10 can have a first longitudinal length which can be the length as measured from the first transverse direction end edge 11 to the second transverse direction end edge 12. In various embodiments, in a first configuration, the absorbent article 10 can have a first transverse width which can be the width as measured from one of the longitudinal side edges 13 to the opposing longitudinal side edge 13. The first longitudinal length and the first transverse width can be any length and width as deemed suitable.

The topsheet layer 20 and the backsheet layer 22 can both extend beyond the outermost peripheral edges of the absorbent core 21 and can be peripherally bonded together, either entirely or partially, using known bonding techniques to form a sealed peripheral region 26. For example, the topsheet layer 20 and the backsheet layer 22 can be bonded together by adhesive bonding, ultrasonic bonding, or any other suitable bonding method known in the art.

In various embodiments, the absorbent article 10 can have a pair of wings 14 extending outwardly, in the transverse direction T, from the absorbent article 10 (such as illustrated in FIG. 1). The wings 14 can drape over the edges of the wearer's undergarment so that the wings 14 are disposed between the edges of the wearer's undergarment and her thighs. The wings 14 can serve at least two purposes. First, the wings 14 can prevent soiling of the wearer's undergarment by forming a barrier along the edges of the undergarment. Second, the wings 14 can be provided with an attachment area 15 in which an attachment aid, such as, for example, a garment attachment adhesive or a hook can be placed, to keep the absorbent article 10 securely and properly positioned in the undergarment. The wings 14 can wrap around the crotch region of the wearer's undergarment to aid in securing the absorbent article 10 to the wearer's undergarment when in use. Each wing 14 can fold under the crotch region of the wearer's undergarment and the attachment aid in each attachment area 15 can either form a secure attachment to the opposite wing 14 or directly to the surface of the wearer's undergarment. In various embodiments, the wings 14 can be an extension of materials forming the topsheet layer 20 and/or the backsheet layer 22, such that the wings 14 can be a unitary construction with the absorbent article 10. In various embodiments, the wings 14 can be constructed of materials similar to the topsheet layer 20, the backsheet layer 22 or combinations of these materials. In various embodiments, the wings 14 can be separate elements bonded to the main body of the absorbent article 10. To maintain the attachment area 15 in a clean configuration until the absorbent article 10 is placed into use by the wearer, the attachment area 15 can be covered by a protective covering 16 such as, for example, a release sheet as is known in the art. It is to be understood that the wings 14 are optional and, in various embodiments, an absorbent article 10 can be configured without wings 14.

The absorbent article 10 can have a protection layer 17. The protection layer 17 can be situated over and engaged with a garment attachment mechanism 31 which can be located on the garment facing surface 25 of the backsheet layer 22. The protection layer 17 can be capable of being at least partially dis-engaged from the garment attachment mechanism 31. The protection layer 17 can be constructed as a laminate having at least one liquid permeable layer 17A and at least one liquid impermeable layer 17B (such as illustrated in FIG. 2). As illustrated in FIGS. 1 and 2, in the first configuration, the liquid permeable layer 17A of the protection layer 17 can face away from the backsheet layer 22 of the absorbent article 10 and the liquid impermeable layer 17B of the protection layer 17 can be in a facing relationship with the backsheet layer 22 of the absorbent article 10.

Each of these components of the absorbent article 10, as well as additional components, will be described in more detail herein.

Topsheet Layer:

The topsheet layer 20 defines a wearer facing surface of the absorbent article 10 that may directly contact the body of the wearer and is liquid permeable to receive body exudates. The topsheet layer 20 is desirably provided for comfort and conformability and functions to direct body exudates away from the body of the wearer, through its own structure, and towards the absorbent core 21. The topsheet layer 20 desirably retains little to no liquid in its structure, so that it provides a relatively comfortable and non-irritating surface next to the tissues within the vestibule of a female wearer.

The topsheet layer 20 can be a single layer of material, or alternatively, can be multiple layers that have been laminated together. The topsheet layer 20 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 20.

In various embodiments, the topsheet layer 20 can be constructed from various nonwoven webs such as meltblown webs, spunbond webs, hydroentangled spunlace webs, or through air bonded carded webs. Examples of suitable topsheet layer 20 materials can include, but are not limited to, natural fiber webs (such as cotton), rayon, bonded carded webs of polyester, polypropylene, polyethylene, nylon, or other heat-bondable fibers, polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 20 can be a bonded carded web made of polypropylene and polyethylene such as that obtainable from Sandler Corporations, Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 20, each of which is hereby incorporated by reference thereto in its entirety. Additional topsheet layer 20 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 20 may contain a plurality of apertures (not shown) formed therethrough to permit body exudates to pass more readily into the absorbent core 21. The apertures may be randomly or uniformly arranged throughout the topsheet layer 20. The size, shape, diameter, and number of apertures may be varied to suit an absorbent article's 10 particular needs.

In various embodiments, the topsheet layer 20 can have a basis weight ranging from about 5, 10, 15, 20 or 25 gsm to about 50, 100, 120, 125 or 150 gsm. For example, in an embodiment, a topsheet layer 20 can be constructed from a through air bonded carded web having a basis weight ranging from about 15 gsm to about 100 gsm. In another example, a topsheet layer 20 can be constructed from a through air bonded carded web having a basis weight from about 20 gsm to about 50 gsm, such as a through air bonded carded web that is readily available from nonwoven material manufacturers, such as Xiamen Yanjan Industry, Beijing DaYuan Nonwoven Fabrics and others.

In various embodiments, the topsheet layer 20 can be at least partially hydrophilic. In various embodiments, a portion of the topsheet layer 20 can be hydrophilic and a portion of the topsheet layer 20 can be hydrophobic. In various embodiments, the portions of the topsheet layer 20 which can be hydrophobic can be either an inherently hydrophobic material or can be a material treated with a hydrophobic coating.

In various embodiments, the topsheet layer 20 can be a multicomponent topsheet layer 20 such as by having two or more different nonwoven or film materials, with the different materials placed in separate locations in the transverse direction T of the absorbent article 10. For example, the topsheet layer 20 can be a two layer or multicomponent material having a central portion positioned along and straddling the longitudinal center direction of the absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 20 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

Backsheet Layer:

The backsheet layer 22 is generally liquid impermeable and is the portion of the absorbent article 10 which faces the garment of the wearer. The backsheet layer 22 can permit the passage of air or vapor out of the absorbent article 10 while still blocking the passage of liquids. Any liquid impermeable material may generally be utilized to form the backsheet layer 22. The backsheet layer 22 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 22 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 22 can be a polyethylene film such as that obtainable from Pliant Corporation, Schaumburg, Ill., USA. Another example can include calcium carbonate-filled polypropylene film. In still another embodiment, the backsheet layer 22 can be a hydrophobic nonwoven material with water barrier properties such as a nonwoven laminate, an example of which can be a spunbond, meltblown, meltblown, spunbond, four-layered laminate. The backsheet layer 22 can, therefore, be of a single or multiple layer construction, such as of multiple film layers or laminates of film and nonwoven fibrous layers. Suitable backsheet layers 22 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Absorbent Core:

An absorbent core 21 can be positioned between the topsheet layer 20 and the backsheet layer 22. The absorbent core 21 can generally be any single layer structure or combination of layer components, which can demonstrate some level of compressibility, conformability, be non-irritating to a wearer's skin, and capable of absorbing and retaining liquids and other body exudates. Additionally, the absorbent core 21 can provide additional capacity to absorb and retain body exudates such as menses. In various embodiments, the absorbent core 21 can be formed from a variety of different materials and can contain any number of desired layers. For example, the absorbent core 21 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 21 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 21 in any amount as desired.

Regardless of the combination of absorbent materials used in the absorbent core 21, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 21 can vary as desired and can comprise any one of various shapes including, but not limited to, triangular, rectangular, dog-bone and elliptical shapes. In various embodiments, the absorbent core 21 can have a shape that generally corresponds with the overall shape of the absorbent article 10. The dimensions of the absorbent core 21 can be substantially similar to those of the absorbent article 10, however, it will be appreciated that the dimensions of the absorbent core 21 while similar, will often be less than those of the overall absorbent article 10, in order to be adequately contained therein.

By way of example, suitable materials and/or structures for the absorbent core 21 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

Protection Layer:

Referring to FIGS. 1 and 2, in a first configuration the protection layer 17 can be situated over and engaged with a garment attachment mechanism 31 which can be located on a garment facing surface 25 of the backsheet layer 22. The protection layer 17 can be capable of being at least partially dis-engaged from the garment attachment mechanism 31. The protection layer 17 can have a longitudinal direction (L), a transverse direction (T), and a depth direction (Z). The protection layer 17 can be constructed as a laminate and can have a liquid permeable layer 17A and a liquid impermeable layer 17B (shown in FIG. 2). In various embodiments, an absorbent material (not shown) can be contained between the liquid permeable layer 17A and the liquid impermeable layer 17B. The protection layer 17 can have a first transverse direction end edge 42, a second transverse direction end edge 41 opposite the first transverse direction end edge 42, and opposing longitudinal direction side edges, 43 and 44. In various embodiments, the protection layer 17 can take on various geometries but will generally have opposing longitudinal direction side edges, 43 and 44, and opposing transverse direction end edges, 41 and 42.

The protection layer 17 can have a longitudinal length which can be the length as measured from the first transverse direction end edge 41 to the second transverse direction end edge 42. The protection layer 17 can have a transverse width which can be the width as measured from a longitudinal direction side edge 43 to the opposing longitudinal direction side edge 44. The longitudinal length and the transverse width of the protection layer 17 can be any length and width as deemed suitable. In various embodiments, the longitudinal length of the protection layer 17 can be substantially the same as the first longitudinal length of the absorbent article 10. In various embodiments, the longitudinal length of the protection layer 17 can be greater than or less than the first longitudinal length of the absorbent article 10. In various embodiments, the transverse width of the protection layer 17 can be substantially the same as the first transverse width of the absorbent article 10. In various embodiments, the transverse width of the protection layer 17 can be greater than or less than the first transverse width of the absorbent article 10. In various embodiments, the longitudinal length and the transverse width of the protection layer 17 can be of a dimension suitable for the protection layer 17 to be fully situated over and cover a garment attachment mechanism 31 positioned on the garment facing surface 25 of the backsheet layer 22 of the absorbent article 10 when the absorbent article 10 is in a first configuration such as illustrated in FIG. 1. In such embodiments, the protection layer 17 can protect the garment attachment mechanism 31 from soiling before the absorbent article 10 is converted from the first configuration to a second configuration whereupon the garment attachment mechanism 31 can be exposed and utilized to maintain the absorbent article 10 securely in position within the wearer's undergarment.

The protection layer 17 can be constructed as a laminate having at least one liquid permeable layer 17A and at least one liquid impermeable layer 17B (such as illustrated in FIG. 2). As illustrated in FIGS. 1 and 2, the liquid permeable layer 17A of the protection layer 17 can face away from the absorbent article 10 in the first configuration and the liquid impermeable layer 17B of the protection layer 17 can be in a facing relationship with the backsheet layer 22 of the absorbent article 10 when the absorbent article 10 is in a first configuration.

The liquid permeable layer 17A can be formed from any material described herein as suitable for the topsheet layer 20. The liquid permeable layer 17A can be a single layer of material, or alternatively, can be multiple layers that have been laminated together. The liquid permeable layer 17A can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a liquid permeable layer 17A.

In various embodiments, the liquid permeable layer 17A can be constructed from various nonwoven webs such as meltblown webs, spunbond webs, hydroentangled spunlace webs, or through air bonded carded webs. Examples of suitable liquid permeable layer 17A materials can include, but are not limited to, natural fiber webs (such as cotton), rayon, bonded carded webs of polyester, polypropylene, polyethylene, nylon, or other heat-bondable fibers, polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable liquid permeable layer 17A can be a bonded carded web made of polypropylene and polyethylene such as that obtainable from Sandler Corporation, Germany.

In various embodiments, the liquid permeable layer 17A can have a basis weight ranging from about 5, 10, 15, 20 or 25 gsm to about 50, 100, 120, 125 or 150 gsm. For example, in an embodiment, a liquid permeable layer 17A can be constructed from a through air bonded carded web having a basis weight ranging from about 15 gsm to about 100 gsm. In another example, a liquid permeable layer 17A can be constructed from a through air bonded carded web having a basis weight from about 20 gsm to about 50 gsm, such as a through air bonded carded web that is readily available from nonwoven material manufacturers, such as Xiamen Yanjan Industry, Beijing DaYuan Nonwoven Fabrics and others.

In various embodiments, the liquid permeable layer 17A can be at least partially hydrophilic. In various embodiments, a portion of the liquid permeable layer 17A can be hydrophilic and a portion of the liquid permeable layer 17A can be hydrophobic. In various embodiments, the portions of the liquid permeable layer 17A which can be hydrophobic can be either an inherently hydrophobic material or can be a material treated with a hydrophobic coating.

The liquid impermeable layer 17B can be formed from any material described herein as suitable for the backsheet layer 22. The liquid impermeable layer 17B can permit the passage of air or vapor out of the absorbent article 10 while still blocking the passage of liquids. Any liquid impermeable material may generally be utilized to form the liquid impermeable layer 17B. The liquid impermeable layer 17B can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the liquid impermeable layer 17B can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a liquid impermeable layer 17B can be a polyethylene film such as that obtainable from Pliant Corporation, Schaumburg, Ill., USA. Another example can include calcium carbonate-filled polypropylene film. In still another embodiment, the liquid impermeable layer 17B can be a hydrophobic nonwoven material with water barrier properties such as a nonwoven laminate, an example of which can be a spunbond, meltblown, meltblown, spunbond, four-layered laminate. The liquid impermeable layer 17B can, therefore, be of a single or multiple layer construction, such as of multiple film layers or laminates of film and nonwoven fibrous layers.

In various embodiments, the protection layer 17 can contain an absorbent material (not shown) positioned between the liquid permeable layer 17A and the liquid impermeable layer 17B. In such embodiments, the absorbent material of the protection layer 17 can be formed from any absorbent material such as, for example, materials described herein as suitable for the absorbent core 21 or fluid intake layer.

The protection layer 17 can be situated over and engaged with a garment attachment mechanism 31 located on a garment facing surface 25 of the backsheet layer 22. The protection layer 17 can be capable of being at least partially dis-engaged from the garment attachment mechanism 31. The garment attachment mechanism 31 can be any operative, conventional attachment mechanism, examples of which can include, but are not limited to, adhesives, cohesives, inter-engaging mechanical fastener systems or the like, as well as combinations thereof. For example, in various embodiments, the garment attachment mechanism 31 can include a garment attachment adhesive. Examples of suitable garment attachment adhesives and patterns include, but are not limited to, those described in DE700225U1, U.S. Pat. No. 3,881,490 to Whitehead, et al., U.S. Pat. No. 3,913,580 to Ginocchio, U.S. Pat. No. 4,337,772 to Roeder, et al., GB1349962, and U.S. Publication No. 2007/0073255 to Thomas, et al., each of which are hereby incorporated by reference thereto in its entirety.

To provide for engagement between the protection layer 17 and the garment attachment mechanism 31, the liquid impermeable layer 17B of the protection layer 17 can be brought into contact with the garment attachment mechanism 31 of the backsheet layer 22. To provide for releasable engagement between the liquid impermeable layer 17B and the garment attachment mechanism 31, the liquid impermeable layer 17B of the protection layer 17 can be provided with a corresponding release component. For example, in various embodiments, the garment facing surface 25 of the backsheet layer 22 can be provided with a garment attachment mechanism 31 in the form of a garment attachment adhesive and the liquid impermeable layer 17B can be at least partially coated with a silicone treatment, as the release component, on the surface of the liquid impermeable layer 17B which, when the absorbent article 10 and protection layer 17 are in a first configuration such as illustrated in FIG. 1, is in a facing relationship with the garment facing surface 25 of the backsheet layer 22. In such embodiments, the silicone treatment on the surface of the liquid impermeable layer 17B which is in a facing relationship with the garment attachment adhesive on the backsheet layer 22 can prevent a permanent engagement between the protection layer 17 and the garment attachment mechanism 31 located on the garment facing surface 25 of the backsheet layer 22 of the absorbent article 10. The protection layer 17, therefore, can be capable of at least partially dis-engaging from the garment attachment mechanism 31.

In various embodiments, the protection layer 17 can be utilized to provide additional area of coverage as deemed suitable by the wearer of the absorbent article 10. The wearer of the absorbent article 10 can manipulate the protection layer 17 to convert the absorbent article 10 from a first configuration to a second configuration. As described herein, the absorbent article 10 can have a first configuration in which the absorbent article 10 can have a first longitudinal length and a first transverse width. In various embodiments, the conversion of the absorbent article 10 from the first configuration to a second configuration can alter at least one of the first longitudinal length and/or first transverse width (in at least one region of the absorbent article) to a second longitudinal length and/or second transverse width.

In various embodiments, such as, for example, in a situation in which the wearer has no desire or need for additional area of coverage beyond the area of coverage already provided by the absorbent article 10 itself, the conversion of the absorbent article 10 from a first configuration to a second configuration can include the steps of fully dis-engaging the protection layer 17 from the garment attachment mechanism 31 of the absorbent article 10 and disposing of the protection layer 17. Following the complete dis-engagement and disposal of the protection layer 17, the absorbent article 10, in the second configuration, can have a second longitudinal length and a second transverse width which, in such embodiments, are the same as the first longitudinal length and the first transverse width of the absorbent article 10 in the first configuration. In such embodiments, as the protection layer 17 has been fully dis-engaged and disposed of, the second longitudinal length of the absorbent article 10 can be measured from the first transverse direction end edge 11 to the second transverse direction end edge 12 of the absorbent article 10 and the second transverse width of the absorbent article 10 can be measured from one of the longitudinal side edges 13 to the opposing longitudinal side edge 13.

Figure 3A:
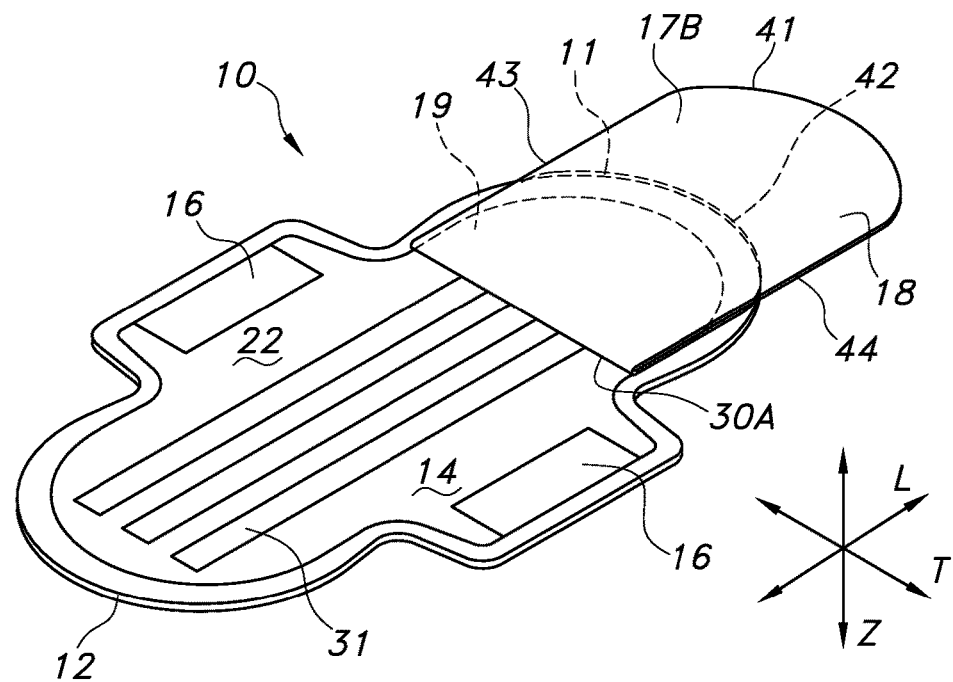
FIG. 3A is a bottom perspective view of an exemplary embodiment of an absorbent article in an embodiment of a second configuration.
Figure 3B:
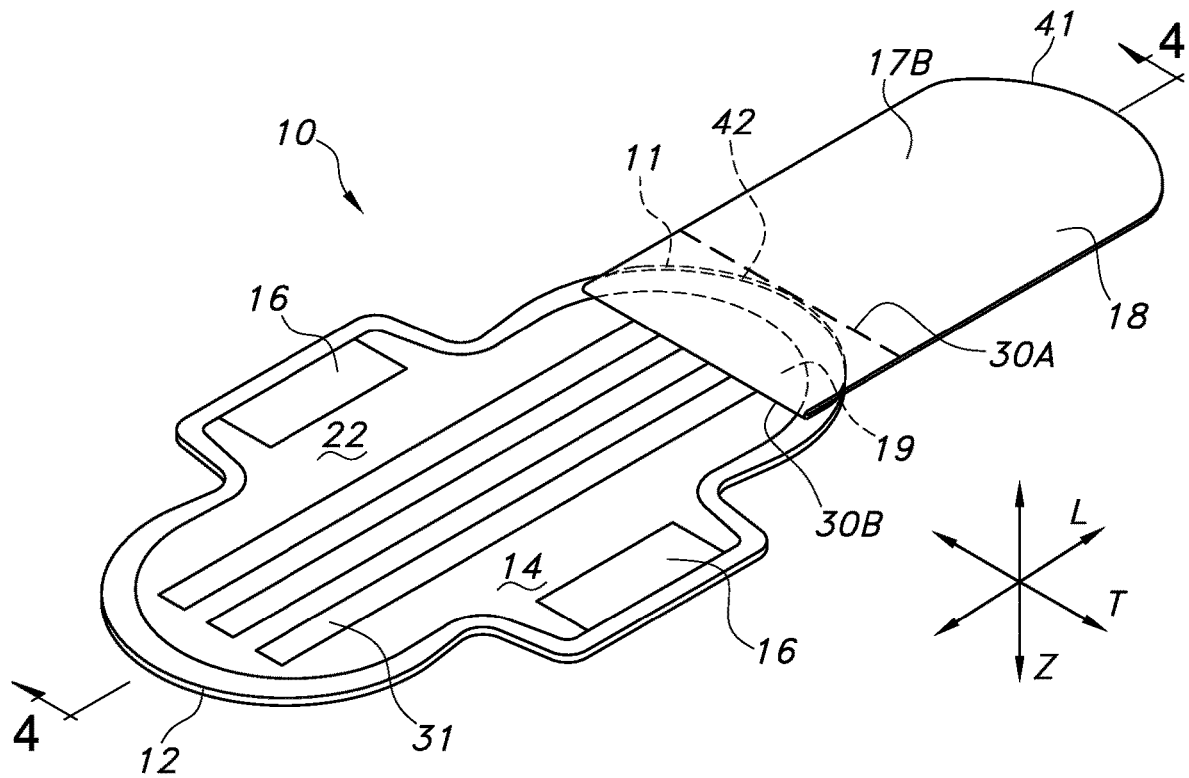
FIG. 3B is a bottom perspective view of an exemplary embodiment of an absorbent article in an embodiment of a second configuration.
Figure 4:
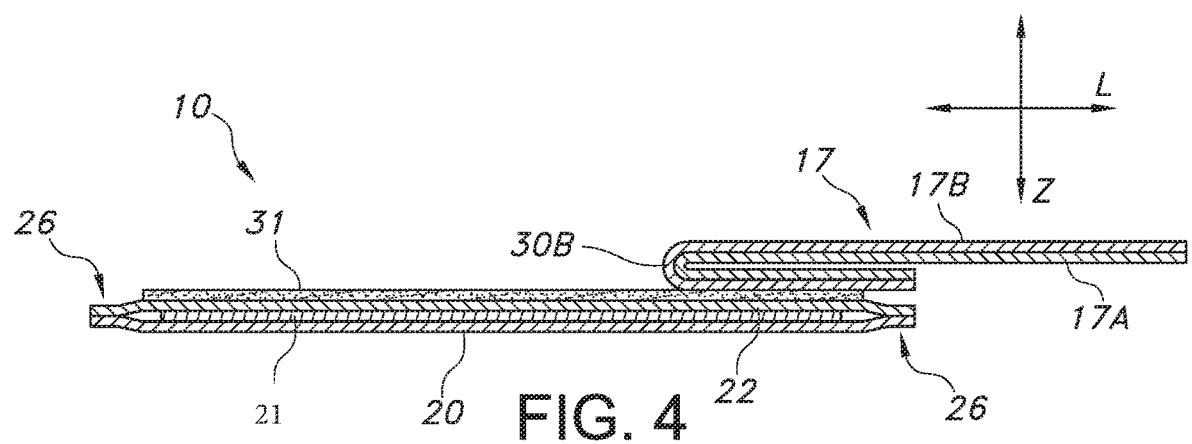
FIG. 4 is a cross-sectional view of the absorbent article of FIG. 3B taken along line 4-4.

Referring to FIGS. 3A and 3B, bottom perspective views of various exemplary embodiments of an absorbent article 10 in a second configuration are illustrated. FIG. 4 provides an illustration of a cross-sectional view of the absorbent article 10 of FIG. 3B taken along line 4-4. In various embodiments, such as illustrated in FIGS. 3A, 3B and 4, the conversion of the absorbent article 10 from a first configuration to a second configuration can include the steps of dis-engaging a portion of the protection layer 17 from the garment attachment mechanism 31 of the absorbent article 10 and folding the dis-engaged portion 18 of the protection layer 17 back and over the remaining engaged portion 19. In such embodiments and as illustrated, at least a portion of the dis-engaged portion 18 of the protection layer 17 can extend beyond a transverse direction end edge, such as transverse direction end edge 11, of the absorbent article 10. In such embodiments, the portion of the dis-engaged portion 18 of the protection layer 17 extending beyond the transverse direction end edge 11 can increase the first longitudinal length of the absorbent article 10 to a second longitudinal length and, therefore, the second longitudinal length of the absorbent article 10 can be greater than the first longitudinal length of the absorbent article 10. The second longitudinal length of the absorbent article 10 can be measured from the transverse direction end edge 41 of the protection layer 17, which extends beyond transverse direction end edge 11 of the absorbent article 10, to the transverse direction end edge 12 of the absorbent article 10.

Referring to the Figures, such as FIGS. 1, 3A, 3B and 4, in various embodiments, the protection layer 17 can be provided with at least one indicator line 30A, and in various embodiments, the protection layer 17 can be provided with additional indicator lines, such as, for example, a second indicator line 30B. The indicator lines, such as 30A and 30B, can provide guidance to the wearer of the absorbent article 10 as to possible locations where a fold in the protection layer 17 can exist following the folding of the dis-engaged portion 18 of the protection layer 17 over the remaining engaged portion 19 of the protection layer 17. The wearer of the absorbent article 10 can select the desired additional area of coverage desired and can dis-engage a portion of the protection layer 17 from the garment attachment mechanism 31, wherein the dis-engaged portion 18 of the protection layer 17 can extend from a transverse direction end edge, such as transverse direction end edge 41, of the protection layer 17 to the desired indicator line, such as indicator line 30A or indicator line 30B. The wearer can then fold the dis-engaged portion 18 of the protection layer 17 back over the remaining engaged portion 19 of the protection layer 17 creating the fold in the protection layer 17 at the corresponding indicator line, such as 30A or 30B. The desired additional area of coverage of protection is thus provided by the portion of the dis-engaged portion 18 of the protection layer 17 which extends beyond the transverse direction end edge 11 of the absorbent article 10. The protection layer 17 can be provided with as many indicator lines, such as 30A and 30B, as desired. The indicator lines, such as 30A and 30B, can be incorporated into the protection layer 17 in any manner deemed suitable, such as, for example, thermal or mechanical embossing, visual cues, such as, for example, graphics, or any other manner deemed suitable. In various embodiments, the indicator lines, such as 30A and 30B, can be incorporated into the protection layer 17 by pre-folding and then un-folding the protection layer 17 prior to engaging the protection layer 17 with the backsheet layer 22. The pre-folding and un-folding of the protection layer 17 can provide the protection layer 17 with lines of flexure which can assist the wearer of the absorbent article 10.

In the embodiment illustrated in FIG. 3A, the protection layer 17 has a pair of opposing transverse direction end edges, 41 and 42, and a portion of the protection layer 17 has been dis-engaged from the garment attachment mechanism 31 beginning with transverse direction end edge 41 of the protection layer 17. As illustrated in FIG. 3A, the protection layer 17 continued to be dis-engaged from the garment attachment mechanism 31 until the desired indicator line 30A was reached and a fold has been created in the protection layer 17 at indicator line 30A following the folding of the dis-engaged portion 18 over the remaining engaged portion 19 of the protection layer. The portion of the dis-engaged portion 18 of the protection layer 17 extending beyond transverse direction end edge 11 of the absorbent article 10 can provide additional area of coverage for the wearer of the absorbent article 10.

In the embodiment illustrated in FIG. 3B, the protection layer 17 has a pair of opposing transverse direction end edges, 41 and 42, and a portion of the protection layer 17 has been dis-engaged from the garment attachment mechanism 31 beginning with transverse direction end edge 41 of the protection layer 17. As illustrated in FIG. 3B, the protection layer 17 continued to be dis-engaged from the garment attachment mechanism 31 until the desired indicator line 30B was reached and a fold has been created in the protection layer 17 at indicator line 30B following the folding of the dis-engaged portion 18 over the remaining engaged portion 19 of the protection layer. The portion of the dis-engaged portion 18 of the protection layer 17 extending beyond transverse direction end edge 11 of the absorbent article 10 can provide additional area of coverage for the wearer of the absorbent article 10.

As can be seen in the illustrations of FIGS. 3A and 3B, while both embodiments illustrated in FIGS. 3A and 3B can provide additional area of coverage to the wearer of the absorbent article 10, the embodiment of the absorbent article 10 illustrated in FIG. 3B can provide a greater additional area of coverage than can the embodiment of the absorbent article 10 illustrated in FIG. 3A. Thus, as demonstrated by the embodiments illustrated in FIGS. 3A and 3B, an absorbent article 10 with a protection layer 17 can be adjusted to the varied needs of wearers of the absorbent article 10. As mentioned herein, the absorbent article 10 can be provided with as many indicator lines, such as 30A and 30B, as deemed suitable, and, therefore, the absorbent article 10 can have additional locations where the dis-engaged portion 18 can be folded over the remaining engaged portion 19.

Figure 5:
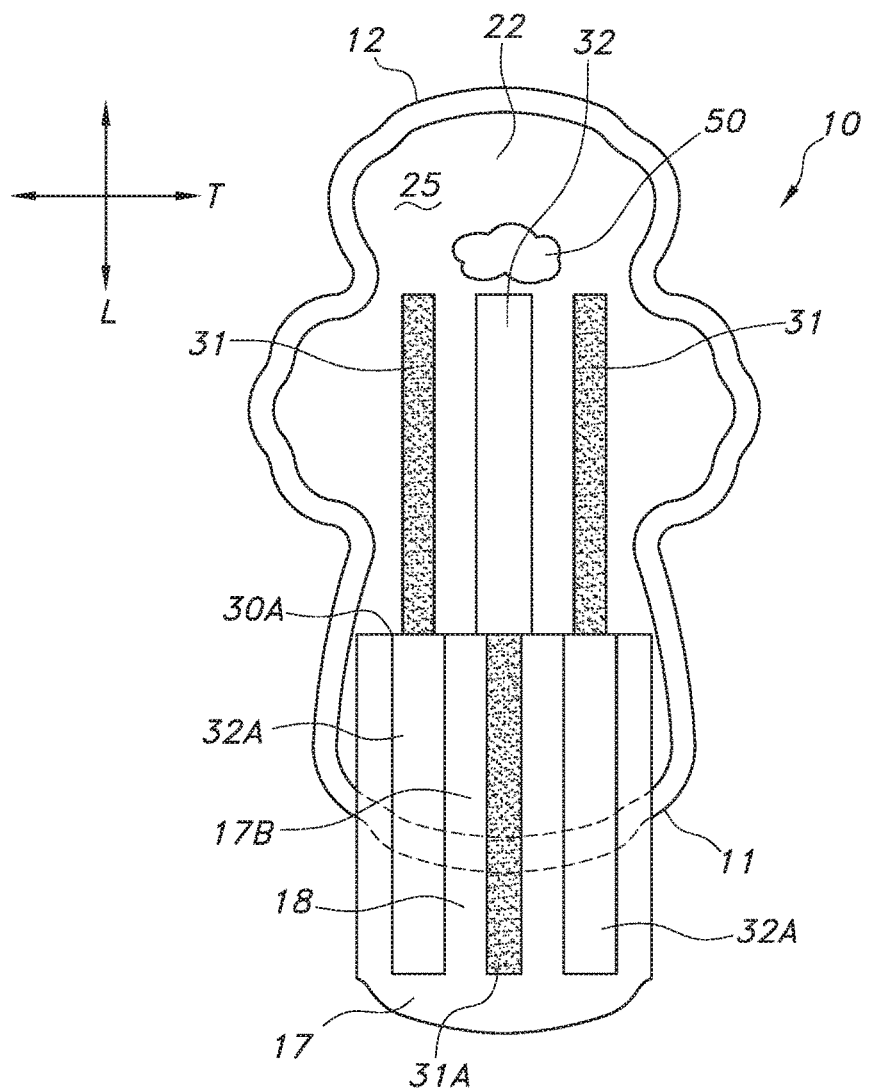
FIG. 5 is a bottom plan view of an exemplary embodiment of an underside of an absorbent article in an embodiment of a second configuration.
Figure 6:
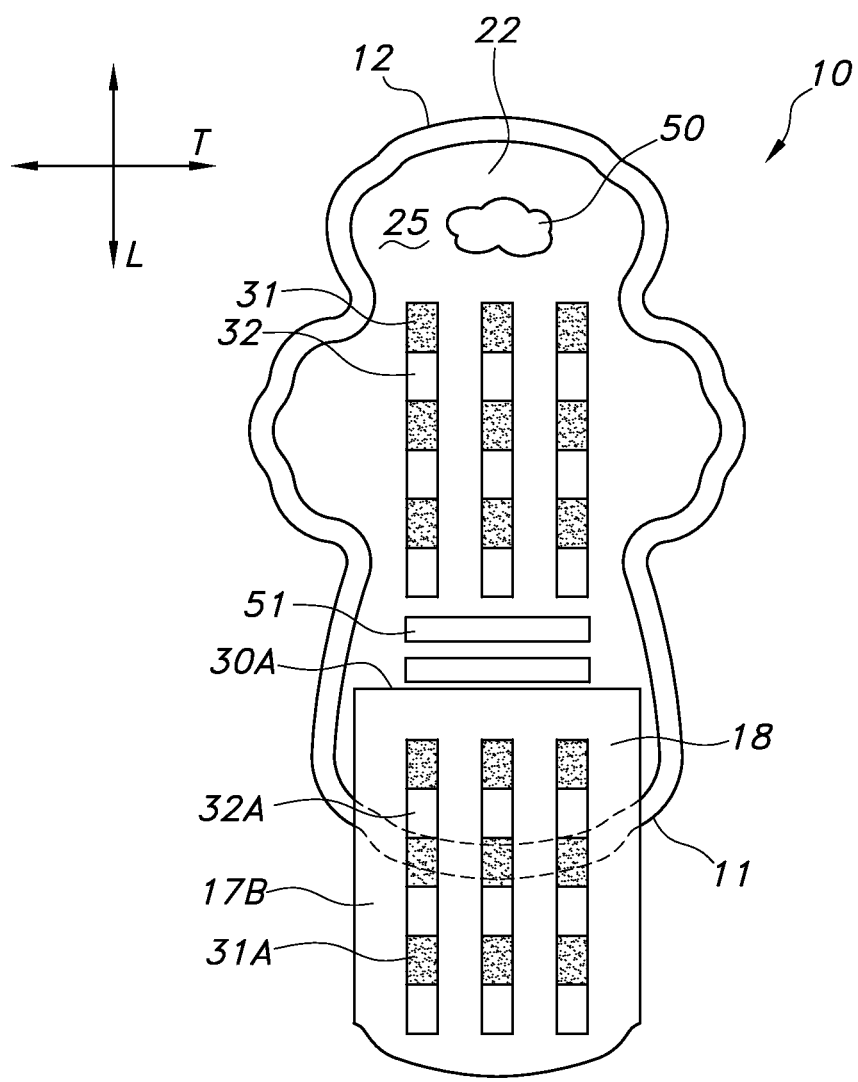
FIG. 6 is a bottom plan view of an exemplary embodiment of an underside of an absorbent article in an embodiment of a second configuration.

Referring to FIGS. 5 and 6, in various embodiments, the liquid impermeable layer 17B of the protection layer 17 can also be provided with a garment attachment mechanism 31A to secure the protection layer 17 to the wearer's undergarment. In various embodiments, each of the garment facing surface 25 of the backsheet layer 22 and the liquid impermeable layer 17B of the protection layer 17 can be provided with a garment attachment mechanism, 31 and 31A, respectively. As with the garment attachment mechanism 31 located on the garment facing surface 25 of the backsheet layer 22, the garment attachment mechanism 31A located on the liquid impermeable layer 17B of the protection layer 17 can be any operative, conventional attachment mechanism, examples of which can include, but are not limited to, adhesives, cohesives, inter-engaging mechanical fasteners, or the like, as well as combinations thereof. For example, in various embodiments, the garment attachment mechanism 31A can include a garment attachment adhesive. Examples of suitable garment attachment adhesives and patterns include, but are not limited to, those described in DE700225U1, U.S. Pat. No. 3,881,490 to Whitehead, et al., U.S. Pat. No. 3,913,580 to Ginocchio, U.S. Pat. No. 4,337,772 to Roeder, et al., GB1349962, and U.S. Publication No. 2007/0073255 to Thomas, et al., each of which are hereby incorporated by reference thereto in its entirety.

In various embodiments in which both the garment facing surface 25 of the backsheet layer 22 and the liquid impermeable layer 17B of the protection layer 17 have a garment attachment mechanism, 31 and 31A, respectively, each of the garment facing surface 25 of the backsheet layer 22 and the liquid impermeable layer 17B of the protection layer 17 can have a corresponding release component which can allow for the garment attachment mechanisms, 31 and 31A, of each of the backsheet layer 22 and the protection layer 17, respectively, to more easily dis-engage from the other layer. Therefore, a release component, such as release component 32, positioned on the garment facing surface 25 of the backsheet layer 22 can allow for a garment attachment mechanism 31A located on the liquid impermeable layer 17B of the protection layer 17 to dis-engage from the backsheet layer 22 of the absorbent article 10. Similarly, a release component, such as release component 32A, positioned on the liquid impermeable surface 17B of the protection layer 17 can allow for the garment attachment mechanism 31 located on the garment facing surface 25 of the backsheet layer 22 to dis-engage from the liquid impermeable layer 17B of the protection layer 17. The release components, 32 and 32A, can prevent permanent adherence between the backsheet layer 22 and the protection layer 17 when the absorbent article 10 and the protection layer 17 are in a first configuration. For example, in various embodiments, the garment facing surface 25 of the backsheet layer 22 can be provided with a garment attachment mechanism 31 in the form of a garment attachment adhesive and the liquid impermeable layer 17B of the protection layer 17 can also be provided with a garment attachment mechanism 31A in the form of a garment attachment adhesive. In such embodiments, each of the garment facing surface 25 of the backsheet layer 22 and the liquid impermeable layer 17B of the protection layer 17 can also be at least partially coated with a silicone treatment as the corresponding release component, 32 and 32A, respectively. In such embodiments, the silicone treatment on the garment facing surface 25 of the backsheet layer 22 can align with a garment attachment adhesive on the liquid impermeable layer 17B of the protection layer 17 and a silicone treatment positioned on the liquid impermeable layer 17B of the protection layer 17 can align with a garment attachment adhesive located on the garment facing surface 25 of the backsheet layer 22. Such alignment can prevent a permanent engagement between the backsheet layer 22 and the protection layer 17.

In various embodiments, the garment attachment mechanisms, 31 and 31A, and their corresponding release components, 32A and 32, can be provided in a pattern arrangement. In various embodiments, the garment attachment mechanisms, 31 and 31A, can be provided in any pattern on the garment facing surface 25 of the backsheet layer 22 and the liquid impermeable layer 17B of the protection layer 17 as deemed suitable. Exemplary patterns can include, but are not limited to, lines, swirls, dots, circles, ovals, and diamonds. In such embodiments, the corresponding release components, 32A and 32, can be provided in a pattern arrangement on the liquid impermeable layer 17B of the protection layer 17 and the garment facing surface 25 of the backsheet layer 22 which can mirror the pattern of the garment attachment mechanism, 31 and 31A, respectively. FIGS. 5 and 6 provide two exemplary and non-limiting examples of pattern arrangements of garment attachment mechanisms, 31 and 31A, and their corresponding release components, 32A and 32, respectively.

FIG. 5 provides a non-limiting illustration of an embodiment of a pattern arrangement of garment attachment mechanisms, 31 and 31A, and corresponding release components, 32A and 32. As illustrated in FIG. 5, the garment facing surface 25 of the backsheet layer 22 can have, extending in the longitudinal direction, lines of garment attachment mechanism 31 and a release component 32. The release component 32 can correspond with a garment attachment mechanism 32A positioned on the liquid impermeable layer 17B of the protection layer 17. In the exemplary embodiment illustrated in FIG. 5, the line of release component 32 can be positioned between lines of garment attachment mechanism 31. While only three total lines are illustrated, two garment attachment mechanism lines 31 and one line of release component 32, it should be realized that more or fewer lines of each of the garment attachment mechanism 31 and release component 32 can be provided on the garment facing surface 25 of the backsheet layer 22. As further illustrated in FIG. 5, a single line of a garment attachment mechanism 31A is positioned between lines of release component 32A on the liquid impermeable layer 17B of the protection layer 17. The lines of release component 32A and the garment attachment mechanism 31A can also extend in the longitudinal direction of the protection layer 17. Each of the lines of release component 32A can correspond with the lines of garment attachment mechanism 31 located on the garment facing surface 25 of the backsheet layer 22. The total number of lines of garment attachment mechanism 31A and release component 32A positioned on the liquid impermeable layer 17B of the protection layer 17 can correspond to the total number of lines, and total number of each, of the garment attachment mechanism 31 and release component 32 positioned on the garment facing surface 25 of the backsheet layer 22. Thus, in the embodiment illustrated in FIG. 5, for the two lines of garment attachment mechanism 31 on the garment facing surface 25 of the backsheet layer 22 two lines of corresponding release components 32A are positioned on the liquid impermeable layer 17B of the protection layer 17 in a corresponding facing relationship. Additionally, for the line of garment attachment mechanism 31A on the liquid impermeable layer 17B of the protection layer 17 a line of a corresponding release component 32 is positioned on the garment facing surface 25 of the backsheet layer 22 in a corresponding facing relationship. The garment attachment mechanisms, 31 and 31A, and the corresponding release components, 32A and 32, respectively, can be arranged in any pattern as deemed suitable. For example, each of the backsheet layer 22 and the protection layer 17 can have any number of lines of garment attachment mechanisms, 31 and 31A, and corresponding release components, 32A and 32, as deemed suitable and the lines can be arranged in any pattern as deemed suitable.

FIG. 6 provides a non-limiting example of an illustration of an embodiment of a pattern arrangement of garment attachment mechanisms, 31 and 31A, and corresponding release components, 32A and 32. As illustrated in FIG. 6, the garment facing surface 25 of the backsheet layer 22 can have multiple lines, extending in the longitudinal direction of the absorbent article 10, of an alternating pattern of garment attachment mechanism 31 and release component 32. The release component 32 can correspond with a garment attachment mechanism 32A positioned on the liquid impermeable layer 17B of the protection layer 17. While only three total lines are illustrated, it should be realized that more or fewer lines can be provided on the garment facing surface 25 of the backsheet layer 22. As illustrated in FIG. 6, the liquid impermeable layer 17B of the protection layer 17 can have multiple lines, extending in the longitudinal direction of the protection layer 17, of an alternating pattern of garment attachment mechanism 31A and release component 32A. The release component 32A can correspond with the garment attachment mechanism 31 positioned on the garment facing surface 25 of the backsheet layer 22. The garment attachment mechanisms, 31 and 31A, and the corresponding release components, 32A and 32, respectively, can be arranged in any pattern as deemed suitable. For example, each of the backsheet layer 22 and the protection layer 17 can have any number of lines of garment attachment mechanisms, 31 and 31A, and corresponding release components, 32A and 32, as deemed suitable and the lines can be arranged in any pattern as deemed suitable. In the embodiment illustrated in FIG. 6, as described herein, a line can extend in the longitudinal direction of the absorbent article 10 and can have an alternating pattern of a garment attachment mechanism, such as garment attachment mechanism 31, and a release component, such as release component 32. Multiple such lines can be arranged side-by-side in the transverse direction of the absorbent article 10. While the pattern of the garment attachment mechanism, such as garment attachment mechanism 31, and release component, such as release component 32, can alternate in the longitudinal direction of the absorbent article 10, they need not, but can, alternate in the transverse direction of the absorbent article 10. Thus, for example, in various embodiments, such as illustrated in FIG. 6, a garment attachment mechanism, such as garment attachment mechanism 31, can be positioned side-by-side with another garment attachment mechanism, such as another garment attachment mechanism 31, in the transverse direction of the absorbent article 10 and a release component, such as release component 32, can be positioned side-by-side with another release component, such as another release component 32, in the transverse direction of the absorbent article. In various embodiments, a garment attachment mechanism, such as garment attachment mechanism 31, can be positioned side-by-side with a release component, such as release component 32, in the transverse direction of the absorbent article 10.

Further illustrated in FIGS. 5 and 6 in non-limiting examples, the garment facing surface 25 of the backsheet layer 22 can be provided with visual cues, such as, for example, placement cues 50 and/or extension cues 51. Placement cues 50 can be incorporated onto the garment facing surface 25 of the backsheet layer 22 to assist the wearer of the absorbent article 10 in determining a location wherein to hold the absorbent article 10 during the conversion of the absorbent article 10 from the first configuration to the second configuration. Extension cues 51 can be incorporated onto the garment facing surface 25 of the backsheet layer 22 to assist the wearer in determining the additional area of coverage which can be provided by the protection layer 17 when a dis-engaged portion 18 has been folded over the remaining engaged portion 19 of the protection layer 17. In various embodiments, the absorbent article 10 can have at least one of indicator lines, such as indicator lines 30A and/or 30B, placement cue 50, extension cues 51, or combinations thereof.

In various embodiments, placement cue 50 can provide an indicator for a location where a wearer of the absorbent article 10 may desire to hold the absorbent article 10 during conversion of the absorbent article 10 from the first configuration to the second configuration. For example, the wearer may desire to grip the absorbent article 10 between their thumb and index finger with the topsheet layer 20 nearest their index finger and the backsheet layer 22 nearest their thumb. In such an example, placement cue 50 may provide an indicator of a suitable placement location for the wearer's thumb during the conversion of the absorbent article 10 from the first configuration to a second configuration. Such a placement can provide improved stability of the absorbent article 10 while it is being manipulated during the conversion from the first configuration to the second configuration. Placement cue 50 can be provided in any manner deemed suitable, such as, for example, but not limited to, thermal or mechanical embossing, graphics, or any other method deemed suitable.

In various embodiments, extension cues 51 can provide guidance to the wearer of the absorbent article 10 as to possible locations where a fold in the protection layer 17 can exist following the folding of the dis-engaged portion 18 of the protection layer 17 over the remaining engaged portion 19 of the protection layer 17. The wearer of the absorbent article 10 can select the desired additional area of coverage and can dis-engage a portion of the protection layer 17 from the garment attachment mechanism 31 until the desired extension cue 51 is visible. The wearer can then fold the dis-engaged portion 18 of the protection layer 17 back over the remaining engaged portion 19 of the protection layer 17 creating a fold in the protection layer 17 at the corresponding extension cue 51. The desired additional area of coverage is then provided by the portion of the dis-engaged portion 18 of the protection layer 17 which extends beyond the transverse direction end edge, such as transverse direction end edge 11, of the absorbent article 10. The garment facing surface 25 of the backsheet layer 22 can be provided with as many extension cues 51 as deemed suitable. Extension cue 51 can be visual and/or textural and can be provided in any manner deemed suitable, such as, for example, but not limited to, thermal or mechanical embossing, graphics, or any other method deemed suitable.

Many currently available commercial absorbent article products utilize a peel strip layer over a garment attachment adhesive to protect the garment attachment adhesive prior to usage of the absorbent article. To prevent contamination of the absorbent article prior to usage, many currently available commercial absorbent article products are contained in an outer wrapper or pouch. Such outer wrapper or pouch can have a construction adhesive located on an inner surface of the wrapper or pouch which can adhere to the peel strip layer situated over the garment attachment adhesive. In such constructions, the adhesion of the construction adhesive to the peel strip layer must be stronger than the adhesion between the peel strip layer and the garment attachment adhesive. The stronger adhesion between the construction adhesive of the wrapper or pouch and the peel strip layer will allow the peel strip layer to remain adhered with the wrapper or pouch when the wearer removes the wrapper or pouch from the absorbent article in advance of using the absorbent article.

In the current disclosure, the absorbent article 10 can have a protection layer 17 which can be a laminate composed of a liquid impermeable layer 17B and a liquid permeable layer 17A. In the first configuration, the liquid impermeable layer 17B is in a face-to-face relationship with the backsheet layer 22 of the absorbent article 10 and the liquid permeable layer 17A faces away from the absorbent article 10. Conventional practices of placing the absorbent article 10 into an outer wrapper or pouch having a construction adhesive thereupon to adhere to the absorbent article 10 will, therefore, not be sufficient as such practices would result in the placement of a construction adhesive material onto the liquid permeable layer 17A of the protection layer 17. Such a configuration is not desired as the liquid permeable layer 17A can come into contact with the skin of the wearer of the absorbent article 10.

Figure 7A:
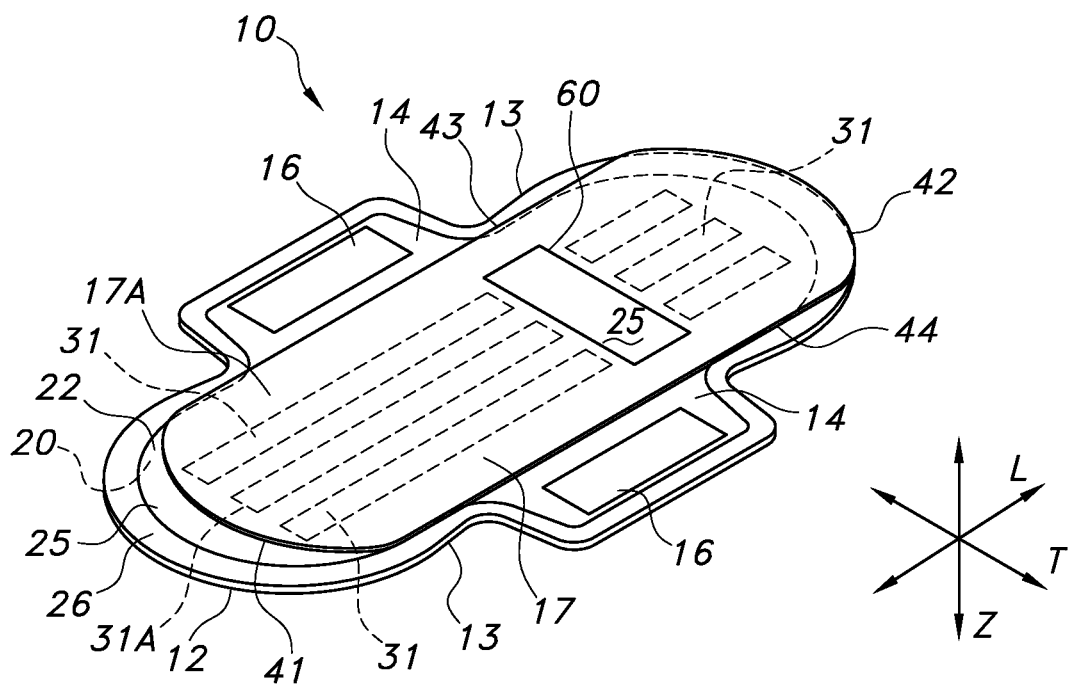
FIG. 7A is a bottom perspective view of an exemplary embodiment of an absorbent article in an embodiment of a first configuration.
Figure 7B:
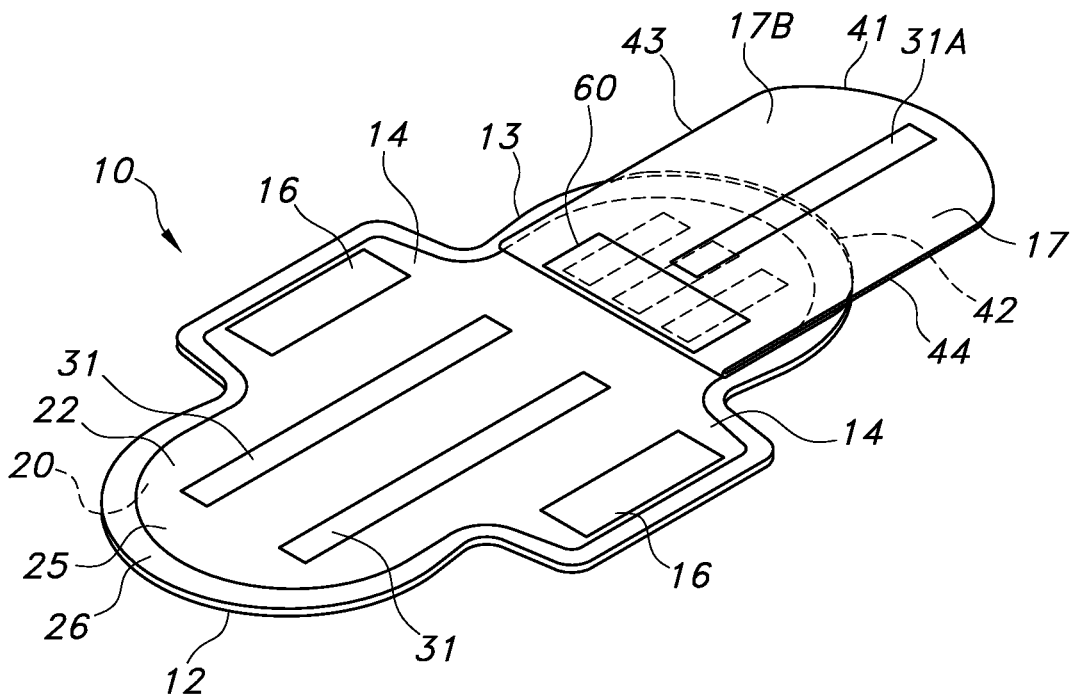
FIG. 7B is a bottom perspective view of an exemplary embodiment of an absorbent article in an embodiment of a second configuration.

Referring to FIGS. 7A and 7B, in various embodiments in which it is desired to place the absorbent article 10 having a protection layer 17 into an outer wrapper or pouch having a construction adhesive on an inside surface of the outer wrapper or pouch for adhering the outer wrapper or pouch to the absorbent article 10, the protection layer 17 can be modified to avoid contact between the liquid permeable layer 17A and the construction adhesive located on the inside surface of an outer wrapper or pouch within which the absorbent article 10 will be placed.

Referring to FIG. 7A, the protection layer 17 can have an open area 60 wherein an overlapping portion of the liquid impermeable layer 17B and the liquid permeable layer 17A have been removed from the protection layer 17. The open area 60 can be a hole in the protection layer 17 through which the garment facing surface 25 of the backsheet layer 22 is accessible and available for contact with a construction adhesive positioned on the inner surface of the outer wrapper or pouch which will enclose the absorbent article 10. In various embodiments, to prevent permanent adhesion between the construction adhesive on the inner surface of the outer wrapper or pouch and the garment facing surface 25 of the backsheet layer 22, a release component, such as, for example, a silicone treatment, can be placed on the garment facing surface 25 of the backsheet layer 22 in the region(s) which will be contacted by the construction adhesive on the inner surface of the wrapper or pouch. For example, one such region of the garment facing surface 25 of the backsheet layer 22 which can have a release component can be the region of the garment facing surface 25 of the backsheet layer 22 which is accessible through the open area 60. Upon removal of the absorbent article 10 from the outer wrapper or pouch, the construction adhesive can dis-engage from the garment facing surface 25 of the backsheet layer 22 allowing for the absorbent article 10 to be further manipulated by the wearer to convert the absorbent article 10 from the first configuration to the desired second configuration.

Referring to FIG. 7B, the absorbent article 10 having a protection layer 17 and an open area 60 within the protection layer 17 is illustrated. In the embodiment illustrated in FIG. 7B, the absorbent article 10 has been converted from a first configuration to a second configuration by dis-engaging a portion of the protection layer 17 from the garment attachment mechanism 31 located on the garment facing surface 25 of the backsheet layer 22. A portion of the garment attachment mechanism 31A located on the liquid impermeable layer 17B of the protection layer 17 has also been at least partially dis-engaged from the garment facing surface 25 of the backsheet layer 22. The dis-engaged portion 18 of the protection layer 17 is illustrated folded over a remaining engaged portion 19 of the protection layer 17. In the embodiment illustrated in FIG. 7B, the open area 60, in the second configuration of the absorbent article 10, can remain underneath the absorbent article 10 and does not extend past a transverse direction end edge, such as transverse direction end edge 11, of the absorbent article 10. By keeping the open area 60 below the absorbent article 10 and not extending beyond transverse direction end edge 11, the wearer of the absorbent article 10 will not experience leakage of body exudates through the open area 60 as they might should a portion the open area 60 extend beyond transverse direction end edge 11 of the absorbent article 10.

In various embodiments, the open area 60 can be incorporated into the protection layer 17 by utilizing a die cut to remove an overlapping portion of the liquid impermeable layer 17B and the liquid permeable layer 17A from the protection layer 17. In such embodiments, as described herein, the construction adhesive on an outer wrapper or pouch can come into contact with the garment facing surface 25 of the backsheet layer 22 through the open area 60 without contacting the liquid permeable layer 17A or the liquid impermeable layer 17B of the protection layer 17. In various embodiments, the open area 60 can be incorporated into the protection layer 17 by utilizing a perforation cutter to incorporate lines of perforations into a portion of the overlapping liquid impermeable layer 17B and the liquid permeable layer 17A. The lines of perforations can enclose a portion of the liquid impermeable layer 17B and the liquid permeable layer 17A. In such embodiments, the construction adhesive on an outer wrapper or pouch can come into contact with at least the portion of the liquid permeable layer 17A enclosed by the lines of perforations. Upon removal of the outer wrapper or pouch, the adherence between the construction adhesive and the liquid permeable layer 17A will be stronger than the adherence between the protection layer 17 and the backsheet layer 22 of the absorbent article 10. The removal of outer wrapper, therefore, will also remove the portion of the protection layer 17 enclosed by the lines of perforations as the lines of perforations will break and the portion of the protection layer 17 which had been enclosed by the lines of perforation will separate from the remainder of the protection layer 17.

Figure 8:
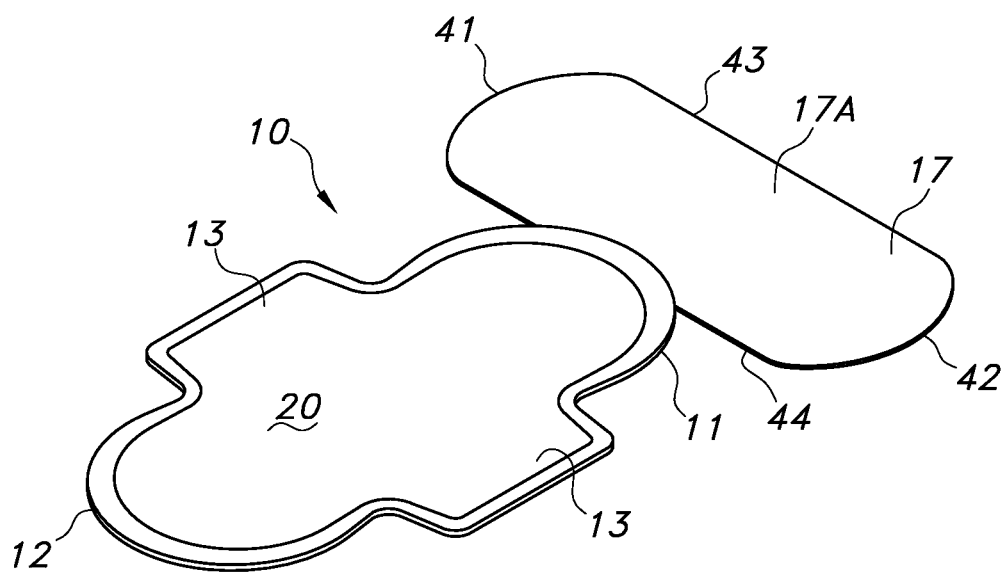
FIG. 8 is a top perspective view of an exemplary embodiment of an absorbent article in an embodiment of a second configuration.

Referring to FIG. 8, a topside view of an embodiment of an absorbent article 10 in a second configuration is illustrated. In various embodiments, the conversion of the absorbent article 10 from a first configuration to a second configuration can include the steps of fully dis-engaging the protection layer 17 from the garment attachment mechanism 31 of the absorbent article 10, orienting the longitudinal direction of the protection layer 17 perpendicular to the longitudinal direction of the absorbent article 10 and re-positioning the protection layer 17 with the absorbent article 10 such that a longitudinal direction side edge, such as longitudinal direction side edge 44, of the protection layer 17 is positioned adjacent to a transverse direction end edge, such as transverse direction end edge 11, of the absorbent article 10. In various embodiments, the protection layer 17 can be provided with its own garment attachment mechanism, such as garment attachment mechanism 31A, which can engage with the wearer's undergarment to maintain the protection layer 17 in place within the wearer's undergarment. In various embodiments, the protection layer 17 can re-engage with the absorbent article 10, such as, for example, a portion of the garment attachment mechanism 31 on the backsheet layer 22 of the absorbent article may engage a portion of the liquid permeable layer 17A of the protection layer 17, to maintain the protection layer 17 in the desired placement in the wearer's undergarment. Such a re-positioning of the protection layer 17 can result in a second longitudinal length of the absorbent article 10 which is greater than the first longitudinal length and a second transverse width of the absorbent article 10, in at least the region of the re-positioning of the protection layer 17 to the absorbent article 10, which is greater that the first transverse width in the same region of the absorbent article 10. The second longitudinal length can be measured from the transverse direction end edge, such as transverse direction end edge 12, of the absorbent article 10 to the furthest longitudinal side edge, such as longitudinal side edge 43, of the protection layer 17. The second transverse width of the absorbent article 10, in at least the region of re-engagement of the protection layer 17 to the absorbent article 10, can be measured as the distance between the opposing transverse direction end edges, 41 and 42, of the protection layer 17. It should be understood that when the protection layer 17 is re-positioned with the absorbent article 10, the topsheet layer 20 of the absorbent article 10 and the liquid permeable layer 17A of the protection layer 17 will both face the wearer of the absorbent article and the backsheet layer 22 of the absorbent article and the liquid impermeable layer 17B of the protection layer 17 will both face the wearer's undergarment.

Figure 9:
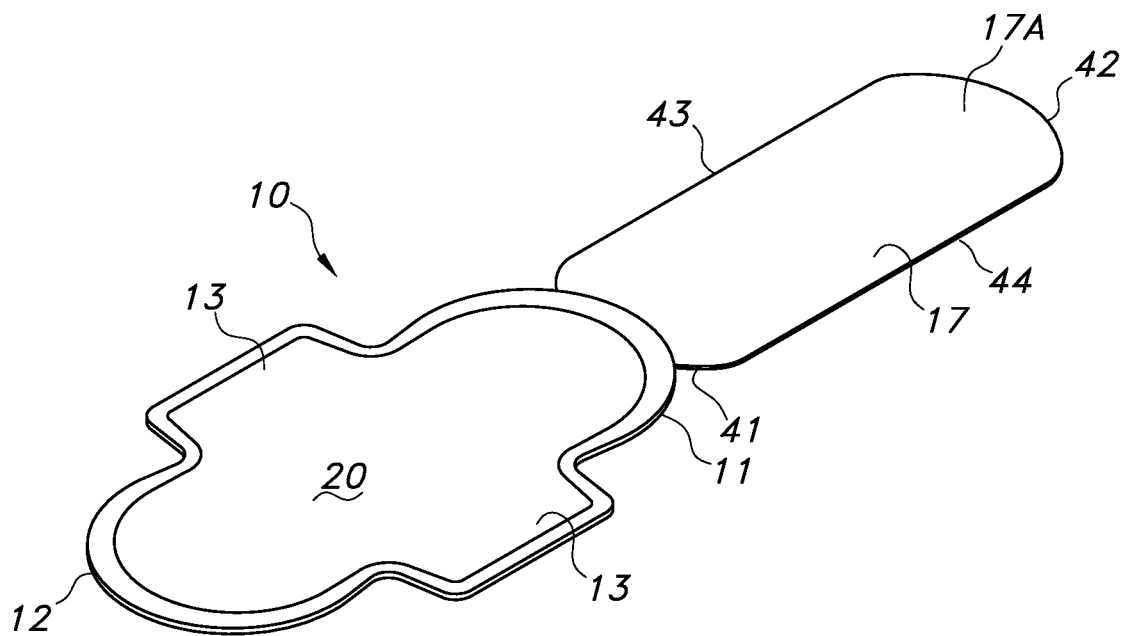
FIG. 9 is a top perspective view of an exemplary embodiment of an absorbent article in an embodiment of a second configuration.

Referring to FIG. 9, a topside view of an embodiment of an absorbent article 10 in a second configuration is illustrated. In various embodiments, the conversion of the absorbent article 10 from a first configuration to a second configuration can include the steps of fully dis-engaging the protection layer 17 from the garment attachment mechanism 31 of the absorbent article 10 and re-positioning the protection layer 17 to the absorbent article 10 by aligning the longitudinal direction of the protection layer 17 with the longitudinal direction of the absorbent article 10 and re-positioning the protection layer 17 with the absorbent article 10 such that a transverse direction end edge, such as transverse direction end edge 41, of the protection layer 17 is positioned adjacent to a transverse direction end edge, such as transverse direction end edge 11, of the absorbent article 10. In various embodiments, the protection layer 17 can be provided with its own garment attachment mechanism, such as garment attachment mechanism 31A, which can engage with the wearer's undergarment to maintain the protection layer 17 in place within the wearer's undergarment. In various embodiments, the protection layer 17 can re-engage with the absorbent article 10, such as, for example, a portion of the garment attachment mechanism 31 on the backsheet layer 22 of the absorbent article may engage a portion of the liquid permeable layer 17A of the protection layer 17, to maintain the protection layer 17 in the desired placement in the wearer's undergarment. The first longitudinal length of the absorbent article 10 is, therefore, increased to a second longitudinal length. The second longitudinal length is thus greater than the first longitudinal length of the absorbent article. The second longitudinal length can be measured as the distance from the transverse direction end edge 12 of the absorbent article 10 to the transverse direction end edge 42 of the protection layer 17. It should be understood that when the protection layer 17 is re-positioned with the absorbent article 10, the topsheet layer 20 of the absorbent article 10 and the liquid permeable layer 17A of the protection layer 17 will both face the wearer of the absorbent article and the backsheet layer 22 of the absorbent article and the liquid impermeable layer 17B of the protection layer 17 will both face the wearer's undergarment.

Figure 10:
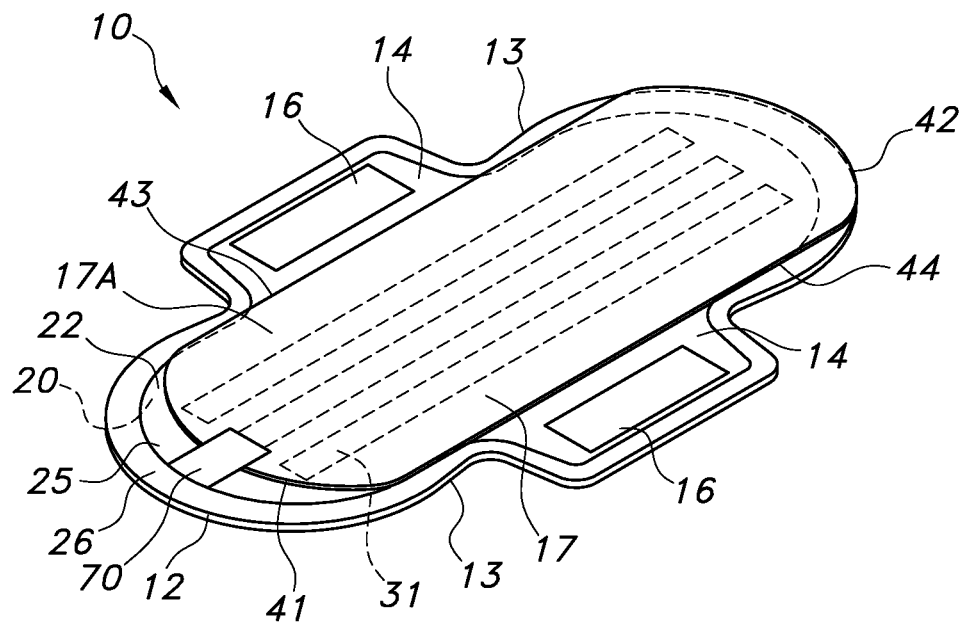
FIG. 10 is a bottom perspective view of an exemplary embodiment of an absorbent article in an embodiment of a first configuration.
Figure 11:
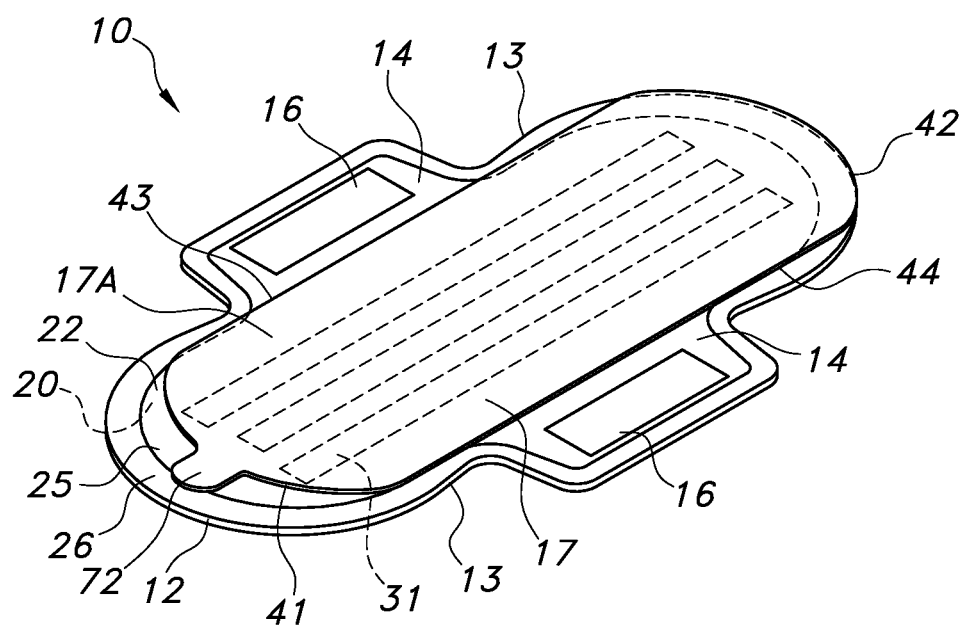
FIG. 11 is a bottom perspective view of an exemplary embodiment of an absorbent article in an embodiment of a first configuration.

In any of the embodiments described herein, to further facilitate conversion of the absorbent article 10 from a first configuration to a second configuration, the protection layer 17 can be provided with a tab, such as, for example tab 70 as illustrated in FIG. 10 or tab 72 as illustrated in FIG. 11. The tab, 70 or 72, can provide an indicator as to a location where a wearer of the absorbent article 10 can begin to dis-engage at least a portion of the protection layer 17 from the garment attachment mechanism, such as garment attachment mechanism 31 positioned on the garment facing surface 25 of the backsheet layer 22. The tab, 70 or 72, can also provide an area of the protection layer 17 for the wearer to grasp when dis-engaging at least a portion of the protection layer 17 from the garment attachment mechanism 31. In various embodiments, tab 70 can be bonded to the protection layer 17, such as illustrated in FIG. 10, in any manner as deemed suitable. In various embodiments, tab 72 can be integral with and an extension of a material of the protection layer 17, such as, for example, an extension of the liquid permeable layer 17A, the liquid impermeable layer 17B, or both the liquid impermeable layer 17B and the liquid permeable layer 17A, such as illustrated in FIG. 11.

Transfer Delay Layer:

In various embodiments, the absorbent article 10 can include a liquid permeable transfer delay layer (not shown) positioned below the topsheet layer 20 in the depth (Z) direction. The transfer delay layer may contain a material that is substantially hydrophobic. For example, the transfer delay layer may be a nonwoven fibrous web composed of relatively hydrophobic materials, such as polypropylene, polyethylene, polyester, or the like, and also may be composed of a blend of such materials. One example of a material suitable for the transfer delay layer can be a spunbond web composed of polypropylene, multi-lobal fibers. Further examples of suitable transfer delay layers can include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al, each of which is hereby incorporated by reference thereto in its entirety.

The transfer delay layer may generally have any size, such as a length of about 150 mm to about 300 mm. Typically, the length of the transfer delay layer can be approximately equal to the length of the absorbent article 10. The width of the transfer delay layer can be from between about 50 mm to about 75 mm. The transfer delay layer can have a basis weight less than about 250 gsm, and in some embodiments, between about 40 gsm and about 200 gsm.

Fluid Intake Layer:

In various embodiments, the absorbent article 10 can include a liquid permeable fluid intake layer (not shown) positioned between the topsheet layer 20 and the absorbent core 21. Such an intake layer can be made of a material that can be capable of rapidly transferring, in the Z-direction, body exudates that are delivered to the topsheet layer 20. The intake layer can generally have any shape and/or size desired. In an embodiment, the intake layer can have a curved rectangular shape, with a length equal to or less than the overall length of the absorbent article 10, and a width less than the width of the absorbent article 10. For example, a length of between about 150 mm to about 300 mm and a width of between about 10 mm to about 60 mm may be utilized. Any of a variety of different materials can be capable of being used for the intake layer to accomplish the above-mentioned functions. The material may be synthetic, cellulosic, or a combination of synthetic and cellulosic materials. For example, airlaid cellulosic tissues may be suitable for use in the intake layer. The airlaid cellulosic tissue may have a basis weight ranging from about 10 gsm to about 300 gsm, and in some embodiments, between about 100 gsm to about 250 gsm. The airlaid cellulosic tissue can be formed from hardwood and/or softwood fibers. An airlaid cellulosic tissue can have a fine pore structure and can provide an excellent wicking capacity, especially for menses.

Additionally, to further enhance the ability of the absorbent article 10 to transfer body exudates in the depth (Z) direction from the topsheet layer 20 toward any lower layers in the absorbent article 10 as well as to enhance the ability of the intake layer to conform to the wearer's body based on its ability to bend, the intake layer can have an opening in the layer which can be any suitable shape, such as ovular, circular, rectangular, square, triangular, etc. The opening in the intake layer can serve to funnel and direct body exudates from the topsheet layer 20 and towards lower layers of the absorbent article 10 in the depth (Z) direction. The opening can also form a cup or well-like structure for holding fluid and preventing its leakage away from a central region of the absorbent article 10 and towards the edges of the absorbent article 10.

Additional Layers:

Additional layers between the topsheet layer 20 and the absorbent core 21 can include surge layers as are commonly known. Surge layers (not shown) can be constructed of any woven or nonwoven material that is easily penetrated by body exudates. The surge layers can help to absorb, decelerate, and diffuse surges or gushes of liquid that may be rapidly introduced into the absorbent article 10. The surge layers can rapidly accept and temporarily hold the liquid prior to releasing the liquid into, for instance, the absorbent core 21 or any other layer of the absorbent article 10. Various woven fabrics and nonwoven webs can be used to construct the surge layers. For example, the surge layers can comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layers can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The surge layers typically have a basis weight of less than about 100 gsm, and in some embodiments, from about 10 gsm to about 40 gsm.

Still another layer that may be present between the topsheet layer 20 and the absorbent core 21 can include a bicomponent fluid distribution layer (not shown), which can increase absorbency by providing a high void space and may be made of a through air bonded carded web, having a basis weight, in an embodiment, of between about 25 gsm and 100 gsm.

Wings:

The wings 14 can be constructed from materials described above with respect to the topsheet layer 20 and the backsheet layer 22. In various embodiments, the wings 14 can comprise an extension of a layer of material within the topsheet layer 20 and/or the backsheet layer 22. By way of example, the wings 14 can be formed by an extension of the topsheet layer 20 and backsheet layer 22 that are then bonded together along peripheral seal 26. Such wings 14 can be integrally formed with the main portion of the absorbent article 10. Alternatively, the wings 14 can be formed independently and separately attached to an intermediate section of the absorbent article 10. Wings 14 that are made independent of the other components of the absorbent article 10 can be bonded to a portion of the topsheet layer 20 and/or backsheet layer 22. Examples of processes for manufacturing absorbent articles 10 and wings 14 include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No., 2004/0040650 to Venturino, et al., and international publication WO1997/040804 to Emenaker, et al., each of which are hereby incorporated by reference thereto in its entirety.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. a first longitudinal length and a first transverse width;
   b. a topsheet layer;
   c. a backsheet layer comprising a garment facing surface, wherein said garment facing surface comprises thereon a first garment attachment mechanism;
   d. an absorbent core between the topsheet layer and the backsheet layer;
   e. a pair of opposing longitudinal direction side edges and a pair of opposing transverse direction end edges;
   f. a protection layer comprising a liquid impermeable layer, a liquid permeable layer, a pair of opposing longitudinal direction side edges and a pair of opposing transverse direction end edges, wherein the liquid impermeable layer of the protection layer comprises thereon a second garment attachment mechanism, and wherein the protection layer is engaged with the first garment attachment mechanism located on the garment facing surface of the backsheet layer; and
   g. a first configuration capable of converting to a second configuration, wherein the liquid impermeable layer of the protection layer is in a facing relationship with the backsheet layer of the absorbent article when the absorbent article is in the first configuration and wherein the protection layer can be fully dis-engaged from the first garment attachment mechanism located on the garment facing surface of the backsheet layer in the conversion of the absorbent article from the first configuration to the second configuration and re-positioned along one of the transverse direction end edges of the absorbent article thereby converting the absorbent article to the second configuration.

2. The absorbent article of claim 1 wherein the protection layer further comprises at least one indicator line.

3. The absorbent article of claim 2 wherein the protection layer is capable of being folded at the at least one indicator line in the conversion of the absorbent article from the first configuration to the second configuration.

4. The absorbent article of claim 1 wherein the protection layer is capable of being re-positioned with the absorbent article such that one of the longitudinal direction side edges of the protection layer is adjacent one of the transverse direction side edge of the absorbent article.

5. The absorbent article of claim 1 wherein the protection layer is capable of being re-positioned with the absorbent article such that one of the transverse direction side edges of the protection layer is adjacent one of the transverse direction end edges of the absorbent article.

6. The absorbent article of claim 1 wherein the protection layer further comprises an absorbent material between the liquid permeable layer and the liquid impermeable layer.

7. The absorbent article of claim 1 wherein the conversion from the first configuration to the second configuration can increase the first longitudinal length to a second longitudinal length.

8. The absorbent article of claim 1 wherein the conversion from the first configuration to the second configuration can increase the first transverse width to a second transverse width.

9. The absorbent article of claim 1 wherein the backsheet layer further comprises a placement cue.

10. The absorbent article of claim 1 wherein the backsheet layer further comprises an extension cue.

11. The absorbent article of claim 1 wherein the protection layer comprises an open area.

12. The absorbent article of claim 1 wherein the protection layer further comprises a tab.

* * * * *